United States Patent [19]

Krause

[11] Patent Number: Plant 6,248

[45] Date of Patent: Aug. 16, 1988

[54] NECTARINE TREE "OLYMPIA"

[76] Inventor: Walter D. Krause, 31671 Indian Guide Rd., Squaw Valley, Calif. 93646

[21] Appl. No.: 902,620

[22] Filed: Sep. 2, 1986

[51] Int. Cl.[4] ..... A01H 5/03

[52] U.S. Cl. ..... Plt./41

[58] Field of Search ..... Plt./41

*Primary Examiner*—Robert E. Bagwill

*Attorney, Agent, or Firm*—Worrel & Worrel

[57] ABSTRACT

A new and distinct variety of nectarine tree denominated varietally as "Olympia" which is somewhat similar to the Red Jim Nectarine Tree (U.S. Plant Pat. No. 4,518) with which it is most closely related, but which is distinguished therefrom, and characterized as to novelty by producing fruit which is mature for commercial harvest approximately September 2 through September 23 at Fresno, Calif.; and which has fruit that has a bright red and glabrous skin; a firm flesh; and noteworthy storage characteristics.

1 Drawing Sheet

BACKGROUND OF THE NEW VARIETY

The present invention relates to a new and distinct variety of nectarine tree, designated varietally as "Olympia", and more particularly to such a nectarine tree which produces fruit which ripens for harvesting from September 2 to September 23, approximately seven days after the Red Jim Nectarine (U.S. Plant Pat. No. 4,518); and which is further distinguished as to novelty by producing fruit whose flesh is firm; the skin of which has a brilliant red and glossy color; and which further produces spherical fruit of substantially uniform size, fruit which exhibit excellent holding quality on the tree and noteworthy storage characteristics after harvest, particularly if under refrigeration.

In a continuing effort to upgrade the quality of his fruit, the applicant is constantly on the alert to locate any new varieties that may appear as chance seedlings in his orchard. In these labors the applicant, in 1981, discovered an open-pollinated seedling which originated from a Royal Giant Nectarine Tree (U.S. Plant Pat. No. 4,107), within the cultivated area of his commercial orchard located at 9284 South Rio Vista Avenue, Reedley, Calif., in the County of Fresno.

ORIGIN

The present variety of nectarine tree was an open-pollinated seedling originating from a Royal Giant Nectarine Tree (U.S. Plant Pat. No. 4,107) within the cultivated area of the commercial orchards under the ownership and control of the inventor at 9284 South Rio Vista Avenue, Reedley, Calif. The subject variety was observed, at that time, to have desirable characteristics and it was thereafter asexually reproduced by the inventor at the same orchard by a bud-graft technique from the original open-pollinated seedling to positions on a fruit bearing Royal Giant Nectarine Tree for the purposes of determining whether the fruit characteristics were true to the original seedling. This first asexual propagation, which occurred in 1981, was continually observed by the inventor, and it has been subsequently determined that the progeny produced possess the same distinctive characteristics as the original open-pollinated seedling.

BRIEF DESCRIPTION OF THE DRAWING

The drawing is a color photograph of a characteristic twig bearing typical leaves, three nectarines showing their external colorations sufficiently mature for harvesting and shipment, a nectarine halved transversely of the suture plane to illustrate the flesh coloration, and a typical stone all of the subject variety.

DETAILED DESCRIPTION

Referring more specifically to the pomological details of this new and distinct variety of nectarine tree, the following has been observed under the ecological conditions prevailing at the orchard of the inventor located in Reedley, Calif. All major color code designations are by reference to the Inter-Society Color Council, National Bureau of Standards. Common color names are also used occasionally.

TREE

Size: Variable, Medium to large.

Vigor: Vigorous.

Figure: Spreading; half-hardy; the new variety is best suited for moderate climates and does not appear well suited for low chill factor or cold winter areas.

Productivity: Very productive; the instant variety is quite fruitful on all bearing parts; annual bearing.

Trunk:

- *Thickness.*—Medium to large; trunk appears to be quite well developed.
- *Texture of bark.*—Coarsely checked.
- *Color.*—Brownish gray; the color of the bark is not distinctive.

Branches:

- *Thickness.*—Medium to large; the new varieties' branches are quite well developed.
- *Texture.*—Coarse.
- *Bark.*—Checked; color — brownish-gray.
- *Lenticels — numbers.*—Few.
- *Lenticels — size.*—Small.

Leaves:

- *Size.*—Medium to large.
- *Length.*—Approximately 6 to 7 inches; (152.4 through 177.8 mm.).
- *Width.*—Approximately 1¼ to 1½ inches; (31.75 through 38.1 mm.).

*Form.*—Lanceolate.
*Color.*—Ventral surface — glossy green; (138. v. d. y. G). Dorsal surface — dull green; (120. m. Y G).
*Texture.*—Ventral surface — no pubescence, glabrous.
*Marginal form.*—Finely serrated along the entire margin.
*Petiole.*—Length — approximately $\frac{5}{8}$ inch; (5.875 mm.).
*Leaf glands.*—Position — opposite. Color — light yellow. Form — reniform. Size — average.
*Stipules.*—None evident.

Flower buds:
*Generally.*—Hardy for nectarine producing areas in California.
*Chilling requirements.*—Approximately 500 hours at temperature below 45° F.
*Form.*—Plump; and rounded at the apex.
*Uniformity.*—Uniform.

Flowers:
*Generally.*—Showy type.
*Petals.*—Large and flat.
*Color.*—Pink; However some deep maroon color may be found at the throat of the blossom.
*Fertility.*—Self-fruitful.
*Flowering period.*—Late February through early March, in Fresno County, Calif.

FRUIT

Maturity when described: For commercial harvesting approximately September 2 through September 23, at Fresno County, Calif.

Size:
*Generally.*—Uniform.
*Axial diameter.*—Approximately $2\frac{3}{4}$ inches; (69.85 mm.).
*Diameter transverse to the suture plane.*—Approximately $2\frac{3}{4}$ inches; (69.85 mm.).
*Diameter transverse to the cheek plane.*—Approximately $2\frac{3}{4}$ inches; (69.85 mm.).
*Form.*—Globose.

Suture: A smooth prominent suture extends from the base to the apex; the suture is well filled and shows no evidence of webbing. The fruit is firm over the entire suture line.
*Ventral surface.*—Uniformly rounded.
*Stem cavity.*—Form — rounded and uniformly flared. Depth — average.

Base: Broad and rounded.
Apex: Uniform; and slightly depressed.
Pistil point: Not evident.

Skin:
*Generally.*—Smooth and glabrous.
*Color.*—Base — yellow, (83 brill Y); remainder of surface — bright red, (13 deep Red).

Stem: Short and stout.

Flesh:
*Color.*—Yellow, (83 brill Y).

*Color of pit well and areas closely adjacent thereto.*—Deep maroon, (14 v. deep Red).
*Texture.*—Uniformly firm.
*Fibers.*—Present; the fibers extend from the pit cavity.
*Ripening.*—Uniform.
*Aroma.*—Present and distinct.
*Eating quality.*—Noteworthy; flavor is subacid and distinct.
*Amygdalin.*—Not present.

Stone:
*Generally.*—Clingstone.
*Form.*—Oblong, and sharply pointed.
*Hilium.*—Oblong, narrow and indented.
*Apex.*—Shape — acuminate and abruptly pointed.
*Sides.*—Uniformity — non-uniform.
*Surface texture.*—Irregularly furrowed and deeply pitted on both sides.
*Ridges.*—Present; moderately rounded and interrupted.
*Ventral edges.*—Form — serrated in shape; and non-uniform.
*Dorsal edge.*—Pronounced, ridged, and non-uniform.
*Color.*—Brown, (46. gy. r Br.); The color of the new variety is uniform over the entire surface.
*Tendency to split.*—Not observed.
*Seed color.*—Brown.
Fertility.—Self-fruitful.

Use: Fresh dessert.

Storage qualities: The new variety has exceptional storage and handling characteristics. Moreover, the new variety is not susceptible to preharvest fruit drop.

Resistance to disease: The instant variety is not particularly susceptible, nor resistant, to nectarine diseases and disorders common to the nectarine producing areas of California.

Although the new variety of nectarine tree possesses the desired characteristics as a result of the growing conditions in Fresno County, Calif., in the central part of the San Joaquin Valley, it is to be understood that variations in the usual magnitude and characteristics incident to growing conditions, fertilization, pruning and pest control are to be expected.

Having thus described and illustrated my new variety of Nectarine Tree, what is claimed as new and desired to be secured by Letters Patent is:

1. A new and distinct variety of nectarine tree substantially as illustrated and described which is somewhat remotely similar to the Royal Giant Nectarine Tree, U.S. Plant Pat. No. 4,107, with which it was discovered as an open-pollinated seedling, but from which it is distinguished by bearing fruit which is mature for commercial harvesting approximately (7) seven days after the Red Jim Nectarine Tree, U.S. Plant Pat. No. 4,518, approximately September 2 through September 23 at Fresno, Calif.; and which furthermore has a brilliant red and glabrous skin; a uniformly firm flesh; and a chilling requirement of at least five hundred hours below 45° F.

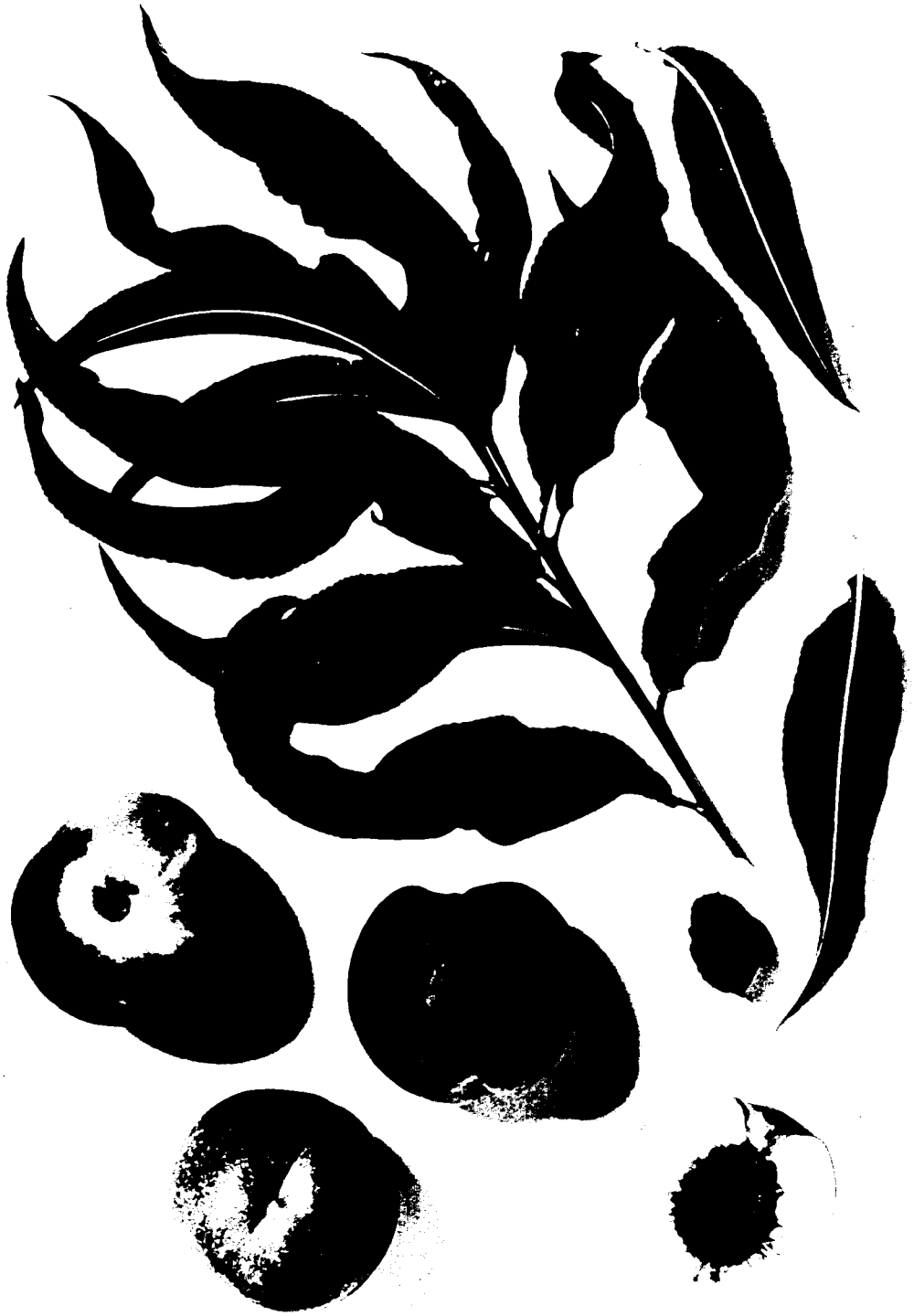

* * * * *